US011583685B2

(12) United States Patent
Irwin et al.

(10) Patent No.: US 11,583,685 B2
(45) Date of Patent: Feb. 21, 2023

(54) SYSTEMS AND METHODS CONFIGURED TO INSERT AN IMPLANT IN AN ABDOMINAL CAVITY

(71) Applicant: Galvani Bioelectronics Limited, Middlesex (GB)

(72) Inventors: Eric Irwin, Collegeville, PA (US); Andrew Hindmarsh, Middlesex (GB); John Bennett, Middlesex (GB)

(73) Assignee: Galvani Bioelectronics Limited, Middlesex (GB)

( * ) Notice: Subject to any disclaimer, the term of this patent is extended or adjusted under 35 U.S.C. 154(b) by 278 days.

(21) Appl. No.: 16/955,362

(22) PCT Filed: Dec. 21, 2018

(86) PCT No.: PCT/GB2018/053767
§ 371 (c)(1),
(2) Date: Jun. 18, 2020

(87) PCT Pub. No.: WO2019/122934
PCT Pub. Date: Jun. 27, 2019

(65) Prior Publication Data
US 2021/0093874 A1 Apr. 1, 2021

Related U.S. Application Data

(60) Provisional application No. 62/609,230, filed on Dec. 21, 2017.

(51) Int. Cl.
*A61N 1/375* (2006.01)
*A61B 17/3209* (2006.01)
(Continued)

(52) U.S. Cl.
CPC .......... *A61N 1/37518* (2017.08); *A61B 17/29* (2013.01); *A61B 17/3209* (2013.01);
(Continued)

(58) Field of Classification Search
CPC .. A61N 1/0504; A61N 1/0507; A61N 1/0509; A61N 1/0551; A61N 1/36;
(Continued)

(56) References Cited

U.S. PATENT DOCUMENTS

2005/0203599 A1 9/2005 Garabedian et al.
2008/0269833 A1 10/2008 Scott et al.
(Continued)

FOREIGN PATENT DOCUMENTS

WO 2005058414 A1 6/2005
WO 2010045407 A1 4/2010
(Continued)

OTHER PUBLICATIONS

International Search Report and Written Opinion, PCT/GB2018/035767, dated Apr. 2, 2018, 12 pp.

*Primary Examiner* — Robert A Lynch
(74) *Attorney, Agent, or Firm* — Banner & Witcoff, Ltd.

(57) ABSTRACT

An implantation system and methods of inserting an implant are disclosed. The method includes the step of making an incision in an abdominal wall with an instrument positioned within an abdominal cavity. The method further includes the steps of forming a pocket between a first surface of the abdominal wall and a second surface of the abdominal wall, such that the incision defines an opening into the pocket, inserting an implant through the opening and into the pocket, and closing the opening such that the implant is captured within the pocket.

17 Claims, 6 Drawing Sheets

(51) Int. Cl.
*A61N 1/378* (2006.01)
*A61B 17/29* (2006.01)
*A61B 18/00* (2006.01)
*A61B 17/00* (2006.01)
*A61B 17/295* (2006.01)

(52) U.S. Cl.
CPC ............ *A61N 1/378* (2013.01); *A61B 17/295* (2013.01); *A61B 2017/00238* (2013.01); *A61B 2018/00529* (2013.01)

(58) Field of Classification Search
CPC .... A61N 1/372; A61N 1/375; A61N 1/37512; A61N 1/37518; A61N 1/3752; A61N 1/3754; A61N 1/3756; A61N 1/3758; A61N 1/378; A61N 1/3956; A61N 1/3968; A61N 1/3975; A61B 17/29; A61B 17/295; A61B 17/3209; A61B 17/32093; A61B 2017/00238; A61B 2018/00529; A61M 60/88
See application file for complete search history.

(56) References Cited

U.S. PATENT DOCUMENTS

2009/0118779 A1    5/2009  Najafi et al.
2011/0172767 A1*   7/2011  Rathi ................. A61B 17/0401
                                                         156/60
2016/0023012 A1    1/2016  Ries et al.

FOREIGN PATENT DOCUMENTS

WO    2011056980 A1    5/2011
WO    2012050998 A1    4/2012

* cited by examiner

SYSTEMS AND METHODS CONFIGURED TO INSERT AN IMPLANT IN AN ABDOMINAL CAVITY

CROSS-REFERENCE TO RELATED APPLICATIONS

This application is a 371 of International Application No. PCT/GB2018/053767, filed Dec. 21, 2018, which claims priority to U.S. Provisional Application 62/609,230, filed Dec. 21, 2017, the contents of both of which are incorporated by reference herein in their entirety.

TECHNICAL FIELD

The present disclosure is related to embodiments of a system including an implant, one or more instruments configured to insert the implant, and a method of inserting the implant into a cavity in a body cavity. More specifically, the present disclosure is directed to embodiments of an implant, one or more instruments configured to insert the implant, and a method of inserting the implant into a pocket in an abdominal wall.

BACKGROUND

Medical devices exist that deliver stimulation to therapeutic targets within a body of a patient. For example, implants, such as pacemakers, deliver stimulation to one or more regions of a heart. Often these medical devices draw power from a power supply to function. Some known implants are implanted subcutaneously within the body of the patient.

U.S. Pat. No. 7,559,900 is directed to a medical device that includes a housing. The housing is subcutaneously implanted outside a patient's ribcage.

U.S. Pat. No. 8,838,234 discloses a method for implanting a subcutaneous defibrillator. The method includes the steps of making an incision in the thorax, through a patient's skin, creating a subcutaneous pathway, and moving a device through the incision into the subcutaneous pathway.

The above examples illustrate existing implants and methods of implantation that include accessing the internal tissues of a body of a patient by piercing the skin. Such approaches can lead to an increased potential for infection. A system configured to be implanted in an intra-abdominal pocket, and a method of implanting the system in an intra-abdominal pocket may result in a decreased potential for infection resulting from the implantation of the system.

SUMMARY

According to an aspect of the disclosure, a method of inserting an implant includes the step of making an incision in an abdominal wall with an instrument positioned within an abdominal cavity. The method further includes the steps of forming a pocket between a first surface of the abdominal wall and a second surface of the abdominal wall, such that the incision defines an opening into the pocket, inserting an implant through the opening and into the pocket, and closing the opening such that the implant is captured within the pocket.

According to an aspect of the disclosure, an implantation system configured to be inserted into a pocket defined by an abdominal wall includes an implant and an attachment mechanism. The attachment mechanism defines an interior space configured to receive the implant, and the attachment mechanism further defines an opening configured to provide passage into the interior space. The opening is further configured to be closed such that when the implant is positioned within the interior space, the implant is prevented from exiting the interior space through the opening and/or intra-abdominal contents are prevented from coming into contact with the implant. The attachment mechanism is configured to be secured to a surface of the abdominal wall defining the pocket.

BRIEF DESCRIPTION OF THE DRAWINGS

The foregoing summary, as well as the following detailed description of illustrative embodiments of the application, will be better understood when read in conjunction with the appended drawings. For the purposes of illustrating the present disclosure, there is shown in the drawings illustrative embodiments. It should be understood, however, that the application is not limited to the specific embodiments and methods disclosed, and reference is made to the claims for that purpose. In the drawings:

DETAILED DESCRIPTION OF ILLUSTRATIVE EMBODIMENTS

Aspects of the disclosure will now be described in detail with reference to the drawings, wherein like reference numbers refer to like elements throughout, unless specified otherwise. Certain terminology is used in the following description for convenience only and is not limiting. The term "plurality," as used herein, means more than one. The terms "a portion" and "at least a portion" of a structure include the entirety of the structure. Certain features of the disclosure, which are described herein in the context of separate embodiments, may also be provided in combination in a single embodiment. Conversely, various features of the disclosure that are described in the context of a single embodiment may also be provided separately or in any subcombination.

Figure 1:
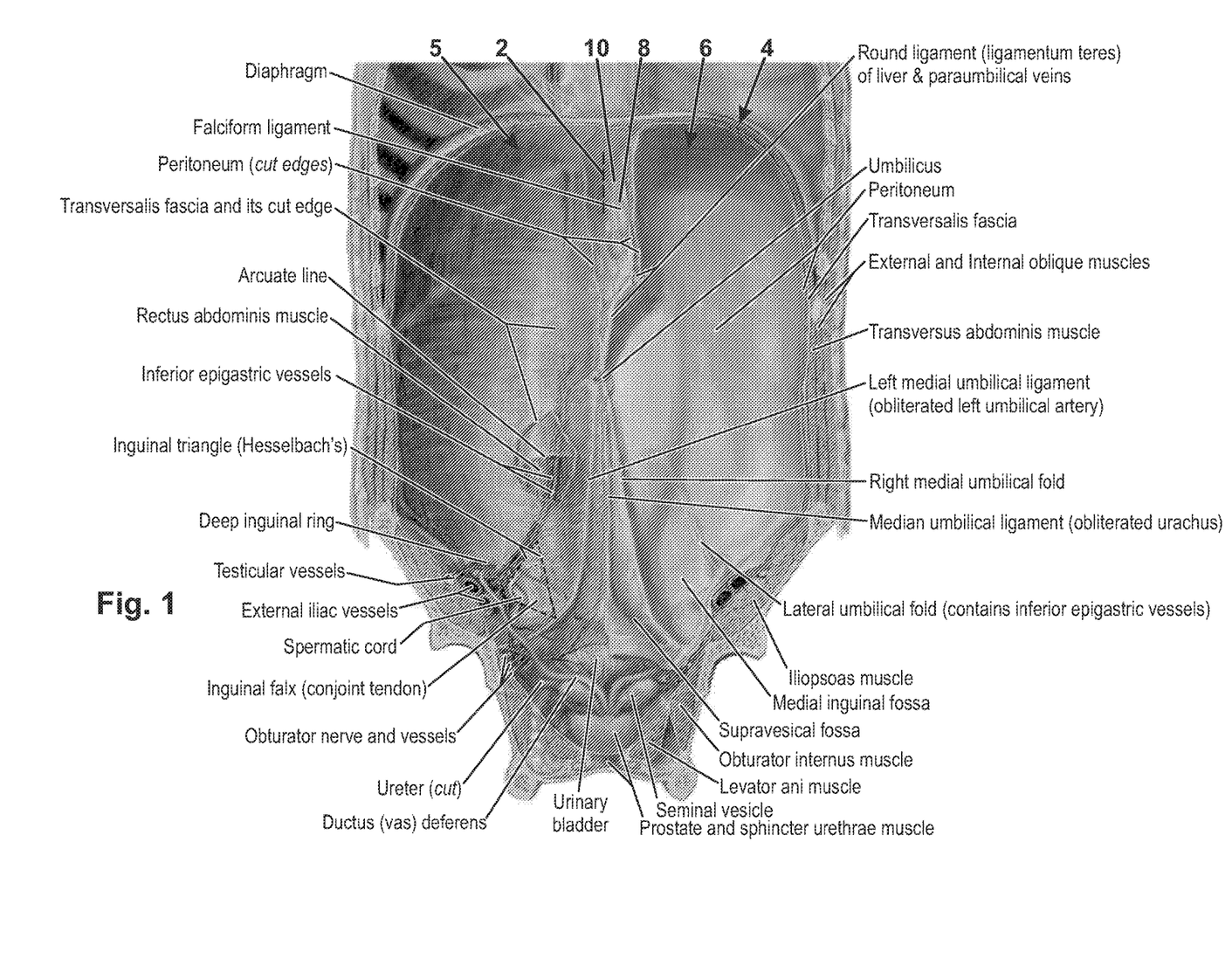
FIG. 1 is a cross-sectional view of an abdominal wall.
Figure 2:
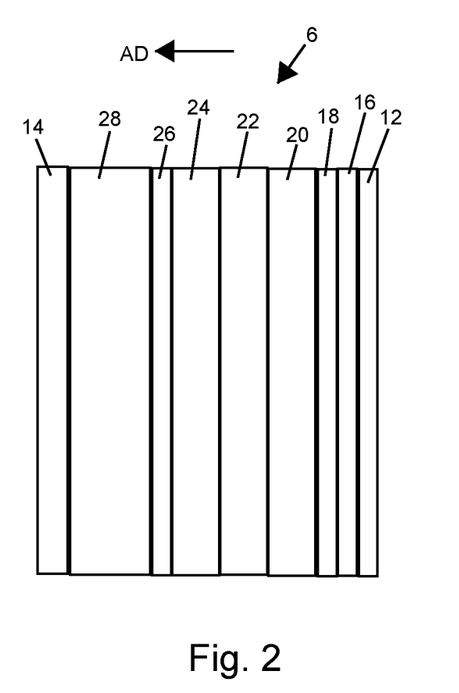
FIG. 2 is a cross-sectional view of layers of the abdominal wall.

Referring to FIGS. 1 and 2, a method of inserting an implant can include the step of making an incision 2 in a biological structure 4. According to one aspect of the disclosure, the biological structure 4 is an abdominal cavity 5, which can include an abdominal wall 6. The abdominal cavity 5 can include a falciform ligament 8, and a liver. The falciform ligament 8 holds the liver in place within the abdominal cavity 5.

The incision 2 can be made at a location 10 on the abdominal wall 6, for example the location 10 can include where the falciform ligament 8 attaches to the abdominal wall 6. The abdominal wall 6 can include a plurality of layers of soft tissue. As shown, the abdominal wall 6 can include, a peritoneal surface 12 and skin 14, the skin 14 spaced from the peritoneal surface 12 in an anterior direction AD. The abdominal wall 6 can further include, in order in the anterior direction AD from the peritoneal surface 12 to the skin 14, extra peritoneal fat 16, endoabdominal fascia 18, transverse abdominus 20, internal oblique 22, external oblique 24, Scarpa's fascia 26, Camper's fascia 28, or any combination thereof, According to one aspect of the disclosure, the step of making the incision 2 includes the step of making the incision 2 in the peritoneal surface 12. The step of making the incision 2 in the peritoneal surface 12 includes the step of terminating the incision 2, with respect to the anterior direction AD, prior to reaching the skin 14. According to one embodiment, the step of making the incision 2 in the peritoneal surface 12 includes the step of terminating the incision 2 with respect to the anterior direction AD, prior to reaching the endoabdominal fascia 18.

Figure 3:
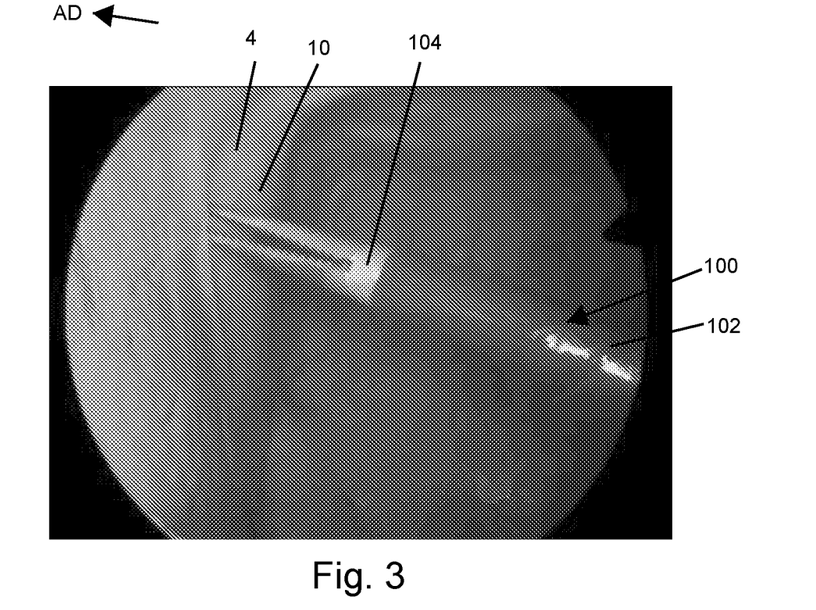
FIG. 3 is a view of an area where the falciform ligament attaches to the anterior abdominal wall.
Figure 4:
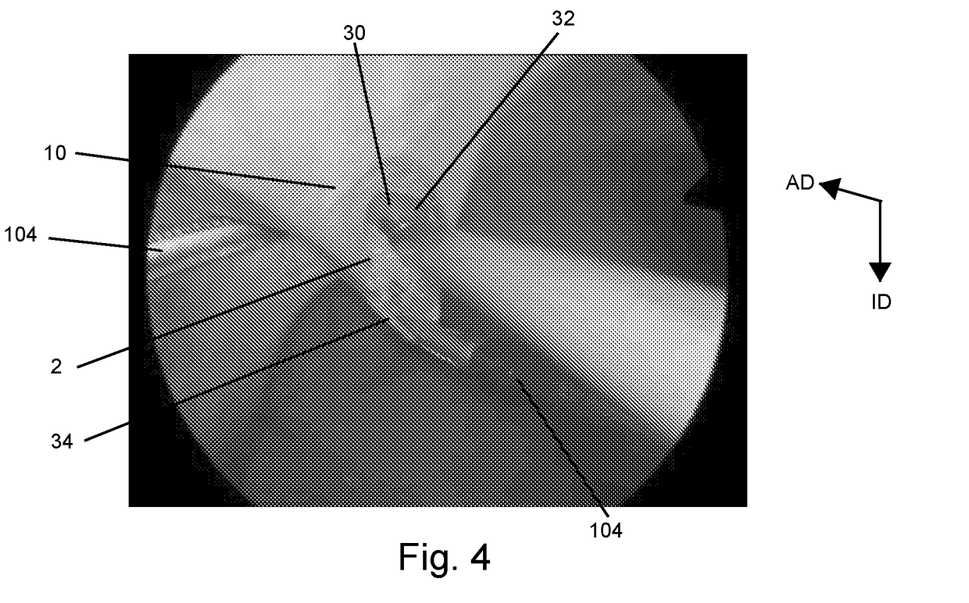
FIG. 4 is a view of a pocket being formed in the area illustrated in FIG. 2.

Referring to FIGS. 3 and 4, an implantation system 100 can include instrumentation 102 configured to form a pocket 30 in the biological structure 4. The instrumentation 102 can include forceps 104, for example endoscopic forceps configured to manipulate the biological structure 4, before, during, and after the incision 2 has been made. The step of making the incision 2 results in an opening 32 being formed. As shown in the illustrated embodiment, the opening 32 can provide passage through the peritoneal surface 12 in the anterior direction AD. The method can include the step of enlarging the opening 32. According to one aspect of the disclosure, the step of enlarging the opening 32 includes the step of manipulating a portion 34 of the peritoneal surface 12 adjacent to the opening 32 and applying a force to the portion 34. As shown, the portion 34 can be adjacent, for example inferior, to the opening 32. The force can be applied via the forceps 104, and can be applied in an inferior direction ID, which is perpendicular to the anterior direction AD, in the posterior direction PD, or both in the inferior direction ID and the posterior direction PD.

Figure 5:
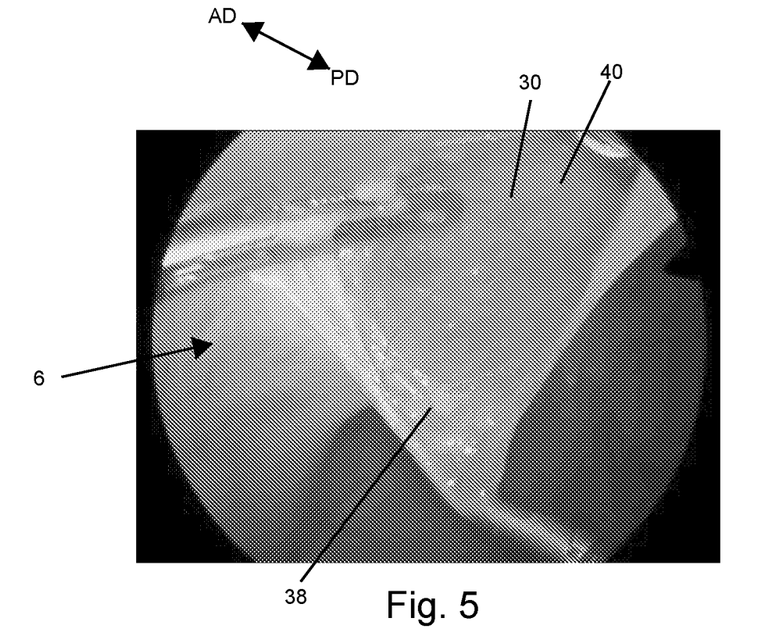
FIG. 5 is a view of the pocket illustrated in FIG. 3, being increased in size.
Figure 6:
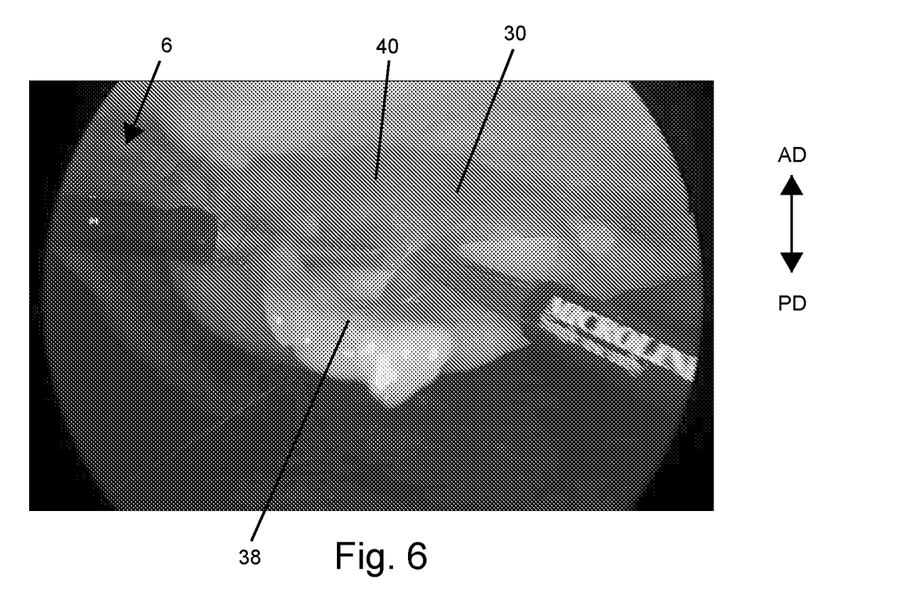
FIG. 6 is another view of the pocket illustrated in FIG. 3, being increased in size.

Referring to FIGS. 5 and 6, the method can include the step of forming the pocket 30. The step of forming the pocket 30 can include the step of moving a first surface 38 of the abdominal wall 6 relative to a second surface 40 of the abdominal wall 6 in a posterior direction PD, which is opposite the anterior direction AD. Alternatively, the step of forming the pocket 30 can include the step of moving the second surface 40 of the abdominal wall 6 relative to the first surface 38 in an anterior direction AD, which is opposite the posterior direction OD. As shown, the step of forming the pocket 30 can include the step of moving the peritoneal surface 12 relative to the skin 14 in the posterior direction PD. The step of forming the pocket 30 can further include the step of moving tissue that is between the peritoneal surface 12 and the skin 14, the step of removing tissue from between the peritoneal surface 12 and the skin 14, or both.

Figure 7:
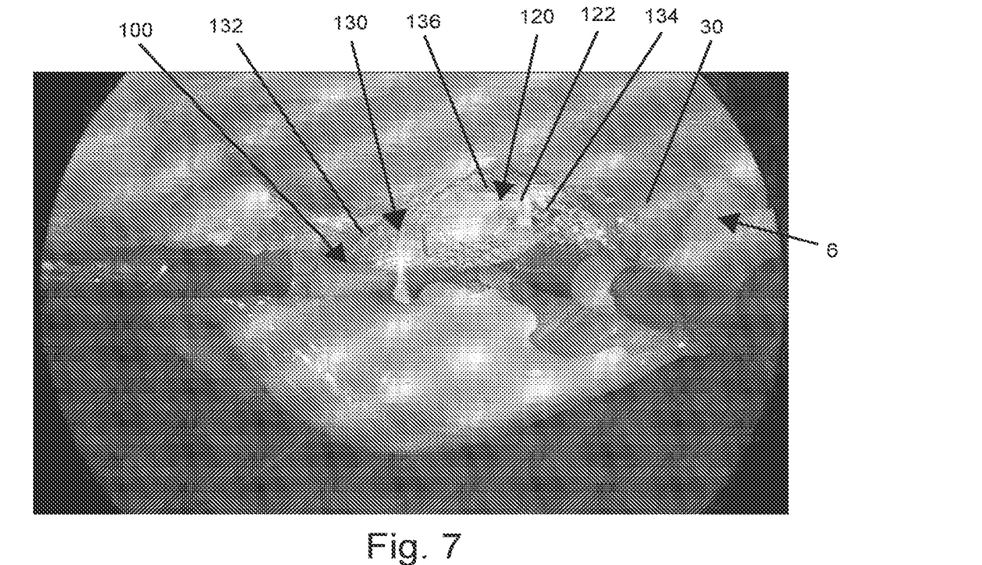
FIG. 7 is a view of an implant being inserted into the pocket illustrated in FIG. 5.
Figure 8:
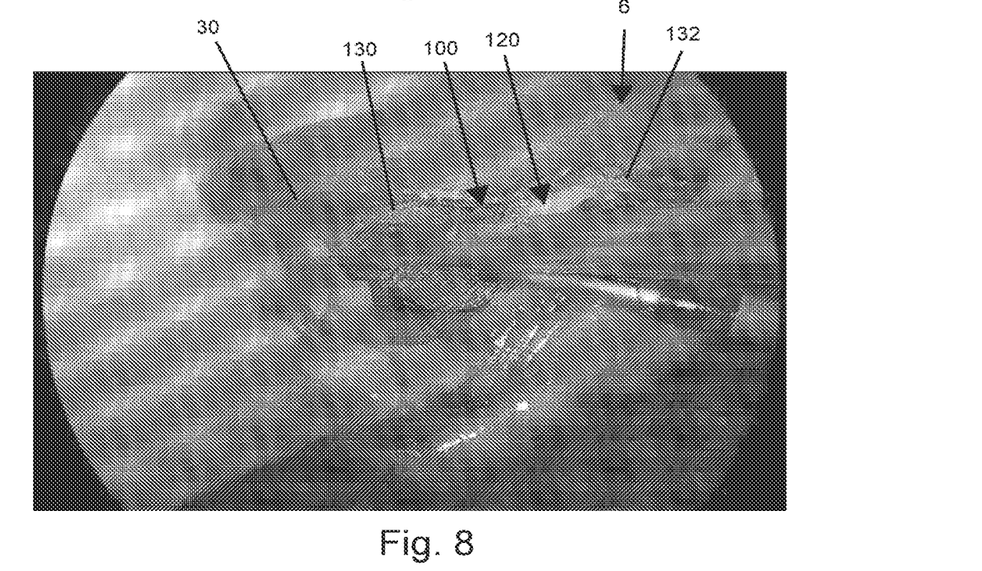
FIG. 8 is a view of the implant and the pocket illustrated in FIG. 6, the implant being attached to the pocket.

Referring to FIGS. 7 and 8, the implantation system 100 can include an implant 120. The implant 120 can include a housing 122 that encloses additional components of the implant 120. The implant 120 can include a power source, an antenna, or both positioned within the housing 122. The power source can include a rechargeable battery configured to receive power from a source remote from the implant 120. For example, the power source can be configured such that when the implant 120 is positioned within the pocket 30, the power source can receive power from a source located outside of the patient's body. According to one aspect of the disclosure, the remote source is not in direct physical contact with the implant 120.

The antenna can be configured to transmit data, receive data, or both. According to one aspect of the disclosure, the antenna can be configured to transmit data about the implant 120, for example an amount of power remaining in the power supply, to a data receiver that is remote from the implant 120. For example, the antenna can be configured such that when the implant 120 is positioned within the pocket 30, the antenna can transmit or receive data from a data receiver or data source located outside of the patient's body. In some embodiments, a plurality of antennae may be provided. In such cases, a first antenna may be provided for communication between the implantation system 100 and the data receiver that is remote from the implant 120; and a second antenna may be provided for wireless charging of the implantation system. Communication between the implantation system 100 and the data receiver may be performed via Bluetooth, for example, or any other suitable communications protocol.

The method can include the step of charging the power supply of the implant 120 from a power source located outside the abdominal cavity of the patient, for example outside the patient's body, while the implant 120 is located in the pocket 30. The method can include the step of sending data to the antenna of the implant 120 from a data source located outside the abdominal cavity of the patient, for example outside the patient's body, while the implant 120 is located in the pocket 30. The method can include the step of receiving data from the antenna of the implant 120 while the implant 120 is located in the pocket 30.

The implantation system 100 can include an attachment mechanism 130 configured to secure the implant 120 within the pocket 30. According to one aspect of the disclosure, the attachment mechanism 130 includes a mesh envelope 132. The attachment mechanism 130 can include an interior space 134 configured to receive the implant 120. The attachment mechanism 130 can further include an opening 136 that defines a pathway into the interior space 134. The attachment mechanism 130 can be configured such that the opening 136 is able to be closed once the implant 120 is positioned within the interior space 134 to prevent removal of the implant 120 from the interior space 134. The attachment mechanism 130 may include at least one suture. Accordingly, the implant 120 (or a part thereof—for example, the mesh envelope 132) may be provided with at least one suture hole, each configured to receive a suture. The implant 120 (or a part thereof—for example, the mesh envelope 132) may be provided with at least one suture tab which extends beyond the main portion of the implant 120 or mesh envelope 132, and/or is positioned at the extremities of the implant 120 or mesh envelope 132. The at least one suture tab may be evenly spaced about the implant 120 or mesh envelope 132. Optionally, each suture tab may have a rectangular opening, which may or may not be the same as the suture hole. Each suture hole may be positioned on a different suture tab. In one example, the attachment mechanism 130 comprises four sutures, and the implant 120 or mesh envelope 132 is provided with four evenly-spaced suture tabs, each having a suture hole which is configured to receive one of the four sutures.

The attachment mechanism 130 can be configured such that when the opening 136 is closed, a pathway is defined to allow a portion of the implant 120 to exit the interior space 134 without allowing the housing 122 to exit the interior space 134. According to one aspect of the disclosure, the implantation system 100, for example the implant 120, can include an electrical cable 140. The implantation system 100 can include an electrode and the electrical cable 140 can be configured to deliver power from the power supply to the electrode.

According to one aspect of the disclosure, the electrical cable extends from the housing 122, and the attachment mechanism 130 is configured to define a pathway for the electrical cable 140 to exit the interior space 134 when the opening 136 is closed. The attachment mechanism 130 can be configured to be secured to a surface of the abdominal wall 6 to secure the implant 120 relative to the abdominal wall 6. As shown in the illustrated embodiment, the attachment mechanism 130 can include a mesh body 138 that is configured to be sutured to a surface of the abdominal wall 6 within the pocket 30. The mesh body 138 can include a plurality of holes configured to allow passage of one or more sutures or other fixation means, such as staples, clips or tacks to secure the attachment mechanism 130 to the abdominal wall 6.

The method can include the step of inserting the implant 120 through the opening 136 of the attachment mechanism 130 and into the interior space 134 of the attachment mechanism 130. The method can include the step of inserting the implant 120, the attachment mechanism 130, or both into the pocket 30. The method can include the step of attaching the implantation system 100 to the abdominal wall 6 when the implantation system 100 is in the pocket 30. According to one aspect of the disclosure, the step of attaching the implantation system 100 to the abdominal wall 6 can include the step of attaching the attachment mechanism 130, with the implant 120 positioned in the interior space 134, to the abdominal wall 6, for example by suturing, tacking (with absorbable tacks, permanent tacks, or both), gluing, or any combination thereof the attachment mechanism 130 to the abdominal wall 6. According to another aspect of the disclosure, the step of attaching the implantation system 100 to the abdominal wall 6 can include the step of attaching the implant 120 directly to the abdominal wall 6, for example by suturing the implant 120 directly to the abdominal wall 6.

The method can include the step of attaching the attachment mechanism 130 to the abdominal wall 6 when the attachment mechanism 130 is in the pocket 30. According to one embodiment, the step of attaching the attachment mechanism 130 to the abdominal wall 6 can include the steps of fixing the implant 120 to the attachment mechanism 130, and fixing the attachment mechanism 130 to the abdominal wall 6. For example, when the attachment mechanism 130 comprises at least one suture and the implant 120 (or a part thereof—for example, the mesh envelope 132) has corresponding suture tabs and suture holes, each suture may be placed through a corresponding suture hole. The suture may then be tied, at its midpoint, to the suture tab. This reduces the risk of the suture being dislodged during subsequent manipulations.

After placement of the sutures, the implant 120 may be held using a laparoscopic tenaculum which is configured to grip the rectangular opening in each of the suture tabs. This is used to guide the implant 120 through the trocar into the abdominal cavity. Then, within the pocket 30, the orientation and position of the implant 120 is determined. This may require placing the implant 120 in the pocket initially. The cranial most extent of the implant 120 is then determined, and incisions, each having a length of 2-3 mm, are made in the skin approximately 2 cm apart. These incisions form at least one opening which correspond to the desired location of the extremities of the implant 120.

A transfascial suture passer, for example a Carter-Thomason suture passer or an EndoClose suture passer, is introduced through each of the openings and advanced through the fascia. For an implant 120 having four suture holes, using two sutures, one end of each suture is placed through a corresponding suture hole on the two cranial most suture tabs. The end of each suture is then grasped and used to draw the implant 120 into the pocket 30. The end of each suture is then clamped above the skin. Next, the suture passer is introduced through the same opening and is passed through the fascia approximately 5 to 10 mm more lateral than the previously placed suture. The second end of each of the sutures is then brought out to this laterally spaced hole. This process may then be repeated on the caudal two most sutures. Similar methods may also be used with different numbers of sutures.

Subsequently, the sutures are tied to secure the implant 120 in place in the pocket 30. The security the implant 120 is confirmed by passing a probe between the fascia and the implant 120. If stability of the implant 120 is deemed satisfactory the sutures are then cut.

In another example, the step of attaching the attachment mechanism 130 to the abdominal wall 6 can include the steps of suturing the implant 120 to the attachment mechanism 130, for example a small section of mesh, and suturing, tacking (with absorbable tacks, permanent tacks, or both), gluing, or any combination thereof the attachment mechanism 130 to the abdominal wall 6. According to one aspect of the disclosure, the attachment mechanism 130 is configured to self-affix or self-retain to the abdominal wall 6 without the use of an additional fixation element.

The method can include the step of closing the opening 136 of the attachment mechanism 130 such that the housing 122 of the implant 120 is prevented from exiting the interior space 134 through the opening 136.

The method can include the step of attaching an electrode to a biological structure, for example a splenic nerve. The method can further include the step of connecting the electrode to power supply of the implant 120, for example by coupling the electrical cable to at least one of the power supply and the electrode.

Figure 9:
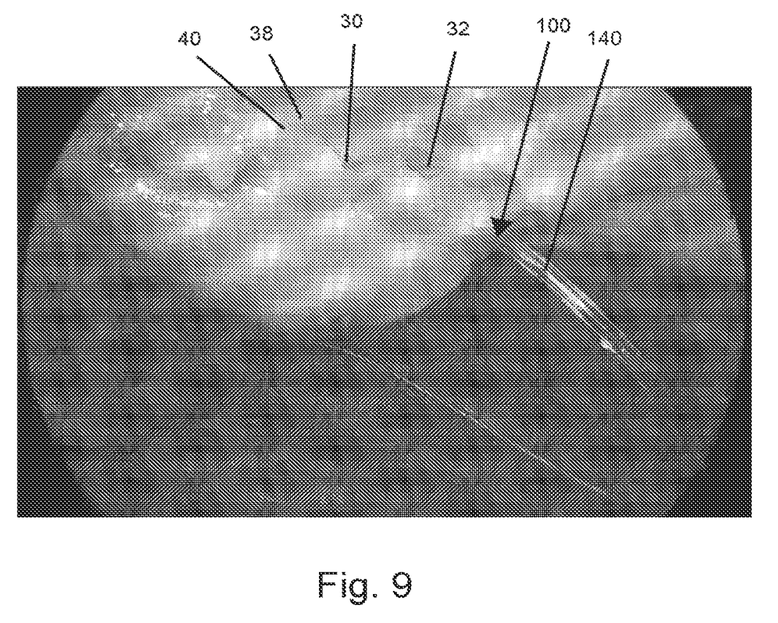
FIG. 9 is a view of the pocket illustrated in FIG. 7, after the implant is attached to the pocket and the pocket is closed.

Referring to FIG. 9, the method can include the step of closing the pocket 30 when the implant 120 is inside the pocket 30, such that the implant 120 is prevented from exiting the pocket 30 through the opening 32. The step of closing the pocket 30 may further include the step of isolating the implant 120, the attachment mechanism 130, or both and any intra-abdominal contents. According to one aspect of the disclosure, the closing step can include tacking the first surface 38 to the second surface 40. The closing step can include the step of providing a pathway for a portion of the implantation system 100 to exit the pocket 30.

As shown in the illustrated embodiment, the closing step includes the step of providing a pathway through which a portion of the implantation system 100, for example the electrical cable, can exit. According to one aspect of the disclosure, the portion of the implantation system 100 that exits the pocket 30 can be positioned at a location used for other intra-abdominal procedures. For example, the portion of the implantation system 100 can be positioned at a location commonly used for setting laparoscopic bands, for example an upper, or superior, portion of a stomach. Positioning the portion of the implantation system 100 in a location used in other procedures can result in an improved long-term safety profile for the implantation of the implantation system 100.

Referring to FIGS. 1 to 9, according to one aspect of the disclosure, the method can be performed in its entirety without making an incision in the skin 14. According to another embodiment, the instrumentation 102 can include a trocar The instrumentation 102 can further include a camera, for example a 5 mm camera, configured to be inserted through the trocar. The method can include the step of discharging a patient from a facility where the implantation was performed within twenty-four hours of completion of the implantation.

The following is a non-exhaustive list of embodiments of the invention, which may or may not be claimed.

1. A method of inserting an implant comprises the steps of: making an incision in an abdominal wall with an instrument positioned within an abdominal cavity; forming a pocket between a first surface of the abdominal wall and a second surface of the abdominal wall, such that the incision defines an opening into the pocket; inserting an implant through the opening and into the pocket; and closing the opening such that the implant is captured within the pocket.

2. The method of embodiment 1, wherein the abdominal cavity includes a falciform ligament, and the step of making the incision includes the step of making the incision in an area where the falciform ligament attaches to the abdominal wall.

3. The method of embodiment 1 or 2, wherein the abdominal wall includes an anterior portion, and the area includes where the falciform ligament attaches to the anterior portion of the abdominal wall.

4. The method of any previous embodiment, wherein the step of forming the pocket includes the step of moving the second surface of the abdominal wall relative to the first surface of the abdominal wall.

5. The method of any previous embodiment, wherein the step of forming the pocket includes the step of moving tissue positioned between the first surface and the second surface within the pocket.

6. The method of any previous embodiment, wherein the step of forming the pocket includes the step of removing tissue positioned between the first surface and the second surface from the pocket.

7. The method of any previous embodiment, further comprising the step of securing the implant to at least one of the first surface and the second surface.

8. The method of any previous embodiment, wherein the step of securing the implant to at least one of the first surface and the second surface includes the step of suturing, tacking, gluing, or any combination thereof, the implant to at least one of the first surface and the second surface.

9. The method of any previous embodiment, further comprising the step of securing the implant to an attachment mechanism.

10. The method of any previous embodiment, wherein the attachment mechanism defines an interior space and an opening configured to provide passage into the interior space.

11. The method of any previous embodiment, further comprising the steps of: moving the implant through the opening and into the interior space; and reducing a size of the opening such that the implant is prevented from exiting the interior space through the opening.

12 The method of any previous embodiment, further comprising the step of securing the attachment mechanism to at least one of the first surface and the second surface.

13. The method of any previous embodiment, wherein the step of securing the attachment mechanism to at least one of the first surface and the second surface includes the step of suturing, tacking, gluing, or any combination thereof, the attachment mechanism to at least one of the first surface and the second surface.

14. The method of any previous embodiment, further comprising the steps of: attaching an electrode to a biological structure; and connecting a power supply of the implant to the electrode.

15. The method of any previous embodiment, wherein the connecting step includes the step of electrically coupling an electrical cable to both the power supply and the electrode.

16. The method of any previous embodiment, wherein the closing step includes the step of defining a pathway for the electrical cable to exit the pocket.

17. The method of any previous embodiment, further comprising the step of transferring power to the power supply from a power source, which is remote from the power supply.

18. The method of any previous embodiment, wherein the transferring step includes transferring power from the power source, which is located such that skin of the abdominal wall, and optionally also one, some or all of subcutaneous tissues, the anterior rectus sheath, the rectus abdominus muscle, the posterior rectus sheath, and tissues located between the peritoneal surface of the falciform ligament and the posterior rectus sheath, is between the power source and the power supply, to the power supply.

19. An implantation system configured to be inserted into a pocket defined by an abdominal wall comprises: an implant; and an attachment mechanism defining an interior space configured to receive the implant, the attachment mechanism further defining an opening configured to provide passage into the interior space, the opening further configured to be closed such that when the implant is positioned within the interior space, the implant is prevented from exiting the interior space through the opening, wherein the attachment mechanism is configured to be secured to a surface of the abdominal wall defining the pocket.

20. The implantation system of embodiment 19, wherein the implant includes a power supply.

21. The implantation system of embodiment 19 or 20, further comprising an electrode and an electrical cable, the electrical cable configured to deliver power from the power supply to the electrode.

22. The implantation system of any one of embodiments 19 to 21, wherein the attachment mechanism is further configured to provide a pathway for the electrical cable to exit the interior space while preventing the implant from exiting the interior space through the opening.

23. The implantation system of any one of embodiments 19 to 22, wherein the attachment mechanism includes a mesh body.

24. The implantation system of any one of embodiments 19 to 23, wherein the implant includes an antenna for transmitting and/or receiving data, and the antenna is configured to transmit data to a receiver, which is remote from the implant.

25. The implantation system of any one of embodiments 19 to 24, wherein the antenna is configured to receive data from a receiver, which is remote from the implant.

26. The implantation system of any one of embodiments 19 to 25, wherein the implant includes an antenna, and the antenna is configured to receive data from a receiver, which is remote from the implant.

27. The implantation system of any one of embodiments 19 to 26, wherein the implant includes an antenna for receiving power, and the antenna is configured to receive power from a power source, which is remote from the implant, for recharging the implant.

28. The implantation system of any one of embodiments 19 to 27, wherein the implant is configured to be inserted laparoscopically, robotically or via open surgery.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the claims.

What is claimed:

1. A method of inserting an implant, the method comprising the steps of:
    making an incision in an abdominal wall with an instrument positioned within an abdominal cavity;
    forming a pocket between a first surface of the abdominal wall and a second surface of the abdominal wall, such that the incision defines an opening into the pocket;
    inserting an implant through the opening and into the pocket; and
    closing the opening such that the implant is captured within the pocket,
    wherein the abdominal cavity includes a falciform ligament, and the step of making the incision includes the step of making the incision in an area where the falciform ligament attaches to the abdominal wall.

2. The method of claim 1, wherein the abdominal wall includes an anterior portion, and the area includes where the falciform ligament attaches to the anterior portion of the abdominal wall.

3. The method of claim 1, wherein the step of forming the pocket includes the step of moving the second surface of the abdominal wall relative to the first surface of the abdominal wall.

4. The method of claim 1, wherein the step of forming the pocket includes the step of moving tissue positioned between the first surface and the second surface within the pocket.

5. The method of claim 1, wherein the step of forming the pocket includes the step of removing tissue positioned between the first surface and the second surface from the pocket.

6. The method of claim 1, further comprising the step of securing the implant to at least one of the first surface and the second surface.

7. The method of claim 6, wherein the step of securing the implant to at least one of the first surface and the second surface includes the step of suturing, tacking, gluing, coagulating or any combination thereof, the implant to at least one of the first surface and the second surface.

8. The method of claim 1, further comprising the step of securing the implant to an attachment mechanism.

9. The method of claim 8, wherein the attachment mechanism defines an interior space and an opening configured to provide passage into the interior space.

10. The method of claim 9, further comprising the steps of:
    moving the implant through the opening and into the interior space; and
    reducing a size of the opening such that the implant is prevented from exiting the interior space through the opening.

11. The method of claim 8, further comprising the step of securing the attachment mechanism to at least one of the first surface and the second surface.

12. The method of claim 11, wherein the step of securing the attachment mechanism to at least one of the first surface and the second surface includes the step of suturing, tacking, gluing, or any combination thereof, the attachment mechanism to at least one of the first surface and the second surface.

13. The method of claim 1, further comprising the steps of:
    attaching an electrode to a biological structure; and
    connecting a power supply of the implant to the electrode.

14. The method of claim 13, wherein the connecting step includes the step of electrically coupling an electrical cable to both the power supply and the electrode.

15. The method of claim 14, wherein the closing step includes the step of defining a pathway for the electrical cable to exit the pocket.

16. The method of claim 13, further comprising the step of transferring power to the power supply from a power source, which is remote from the power supply.

17. The method of claim 16, wherein the transferring step includes transferring power from the power source, which is located such that skin of the abdominal wall, and optionally also one, some or all of subcutaneous tissues, the anterior rectus sheath, the rectus abdominus muscle, the posterior rectus sheath, and tissues located between the peritoneal surface of the falciform ligament, the posterior rectus sheath, aponeuroses of the oblique muscle layers and the transversus abdominis muscle, is between the power source and the power supply, to the power supply.

* * * * *